(12) United States Patent  
Tai et al.

(10) Patent No.: US 6,698,798 B2
(45) Date of Patent: Mar. 2, 2004

(54) MICROMACHINED RUBBER O-RING MICROFLUIDIC COUPLERS

(75) Inventors: Yu-Chong Tai, Pasadena, CA (US); Tze-Jung Yao, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 0 days.

(21) Appl. No.: 09/835,299

(22) Filed: Apr. 12, 2001

(65) Prior Publication Data

US 2002/0093143 A1 Jul. 18, 2002

Related U.S. Application Data

(60) Provisional application No. 60/197,151, filed on Apr. 13, 2000.

(51) Int. Cl.[7] ............................. F16J 15/02; F16L 39/00
(52) U.S. Cl. .................. 285/124.1; 285/124.3; 285/345
(58) Field of Search ...................... 285/124.1, 124.2, 285/124.3, 124.4, 124.5, 345

(56) References Cited

U.S. PATENT DOCUMENTS

| | | | | |
|---|---|---|---|---|
| 4,474,889 A | * | 10/1984 | Terry et al. | ............... 436/161 |
| 5,640,995 A | | 6/1997 | Packard et al. | |
| 5,964,239 A | * | 10/1999 | Loux et al. | .................... 137/15 |
| 6,077,053 A | | 6/2000 | Fujikawa et al. | |
| 6,103,199 A | | 8/2000 | Bjornson et al. | |
| 6,209,928 B1 | * | 4/2001 | Benett et al. | ............. 285/124.1 |
| 6,242,324 B1 | | 6/2001 | Kub et al. | |
| 6,251,343 B1 | | 6/2001 | Dubrow et al. | |
| 6,273,478 B1 | * | 8/2001 | Benett et al. | ............... 285/346 |
| 6,488,315 B1 | * | 12/2002 | Brenner et al. | ........... 285/124.5 |

* cited by examiner

Primary Examiner—Lynne H. Browne
Assistant Examiner—Giovanna Collins
(74) Attorney, Agent, or Firm—Fish & Richardson P.C.

(57) ABSTRACT

A micromachined O-ring is described. The O-ring can be formed for use in micromachined microfluidic devices.

11 Claims, 3 Drawing Sheets

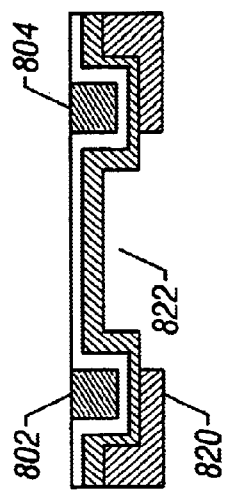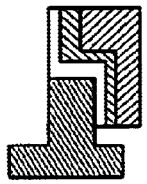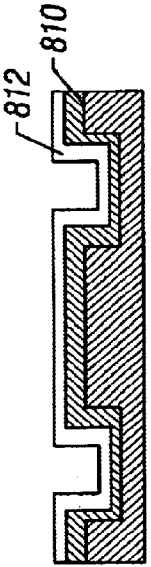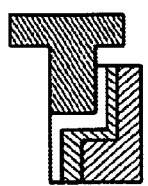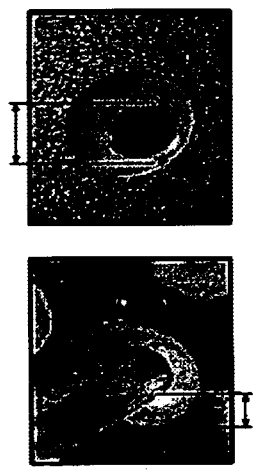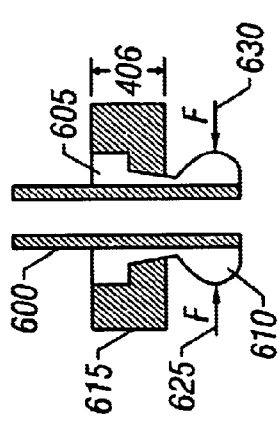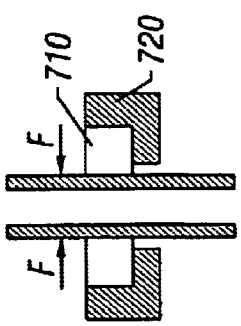

MICROMACHINED RUBBER O-RING MICROFLUIDIC COUPLERS

CROSS-REFERENCE TO RELATED APPLICATIONS

This application claims benefit of U.S. Provisional Application No. 60/197,151, filed Apr. 13, 2000.

BACKGROUND

Microfluidics allow small sized elements to be used to move fluids from one area to another. Microfluidic handling devices may include micro pumps, micro valves, micro heat exchangers, micro mass spectrometers, micro chromatographs, and micro mixers, and others. Many microfluidic systems, however, require connections. For example, the system as described above may require a connection to a fluidic reservoir.

Many techniques have been proposed to connect a macro fluidic system, such as a fluid reservoir, to a microfluidic system, such as a micromachined fluid handling element. Some interconnection schemes may use conventional precision machining in an attempt to clamp together the various parts of a microfluidic system. This technique, however, may require a large amount of conventional machining.

Other techniques achieve interconnection by gluing capillaries into micromachined pits fabricated by isotropic etching or anisotropic etching of the silicon substrate. This technique may have a low yield because of the tendency for the inlet and outlets to be blocked by the excess glue.

Injection molding has also been suggested. However, the injection molding process may be complex.

SUMMARY

The present system teaches an microfluidic coupler formed using micromachining techniques. An embodiment describes a coupler which is annular in shape, and is referred to as an "O" ring. The O-ring may be made of any of a number of different kinds of rubber materials.

The use of a rubber O-ring of this type allows capillaries to connect to external macro fluidic systems. The connections from the macro fluidic systems can be directly connected into the microfluidic devices. The system disclosed herein allows a coupling force which is strong enough to withstand high pressure, but yet does not require glue or mechanical clamping.

Another embodiment defines a selectively connectible and disconnectable assembly.

BRIEF DESCRIPTION OF THE DRAWINGS

These and other aspects will now be described in detail with reference to the accompanying drawings, wherein:

FIGS. 5A and 5B show photographs of the O-ring and their diameter;

FIG. 6 shows a first embodiment of the O-ring and its sealing technique;

FIGS. 7 shows a second embodiment O-ring and its sealing behavior;

FIGS. 8A–8F show a technique of forming the O-ring as disclosed herein;

DETAILED DESCRIPTION

Figure 1:
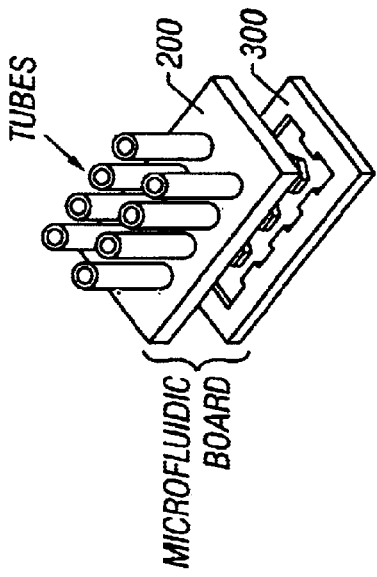
FIGS. 1–3 show views of microfluidic boards, effectively forming connector assemblies.
Figure 2:
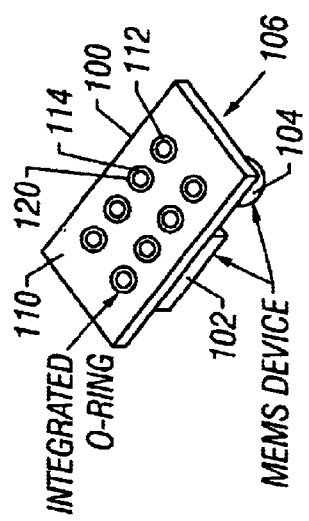
Figure 3:
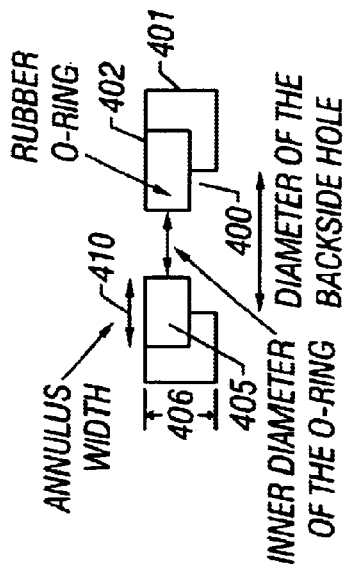

FIGS. 1–3 show an embodiment of a system using the techniques of the present invention. The disclosed system includes a plurality of capillaries formed in a specified spacing, to connect with a board that includes a plurality of integrated micromachined connector parts, having the same spacing. This system enables the capillaries to integrate as a connector and provide a good seal. The description describes annular shaped O rings, although the term should be understood to encompass other shapes of sealing rings which are fluid tight connectors having the characteristics described herein.

Board 100 is a MEMS microfluidic device, which, as conventional, can be formed by micromachining techniques using a semiconductor substrate. The board includes MEMS devices 102, 104 on a first surface 106 thereof. In the view of FIG. 1, the first surface 106 is shown facing downward, so that the connection surface 110 can be easily seen. The connection surface includes a plurality of connection ports such as 112, 114. Each connection port such as 114 includes an integrated o-ring coupled thereto.

FIG. 2 shows an exploded view of the assembly. A second board 200 has with capillaries 202 extending below the surface of the device. The end 204 of capillary 202 connects to the connection port 206 on board 100, and is connected to O-ring 208 on connection part 206. The board 102 which includes the O rings may also be in contact with another microfluidic channel board 220. This board 220 may include channels thereon, or may include a macro fluidic reservoir.

FIG. 3 shows the rear view of the board 200, showing a view of the capillaries. As in the above, this may include an assembled macrofluidic board 300.

In any of these devices, the device can be attached and detached as needed. This allows the microfluidic system to be rearranged to include different boards such as 200. Different microfluidic devices can be plugged in to the different connector locations. In this way, the couplers act as quick connect type couplers, which are reusable, preferably without adhesive connection.

This system uses a different kind of paradigm than is currently in use. Many of the inlet and outlets in current microfluidic systems are rectangular in shape; and may be formed by anisotropic etching of silicon in a substrate. For example, the inlet and outlets in a fluidic system may be etched into a (100) silicon wafer using in an isotropic wet-etch solution such as KOH, TMAH and/or EDP. The etching may be carried out through a square opening in the etching mask. While the shape of the rubber o-ring couplers described in the present specification are not limited to being annular, they can be properly changed to various sizes at inlets and outlets.

Figure 4:
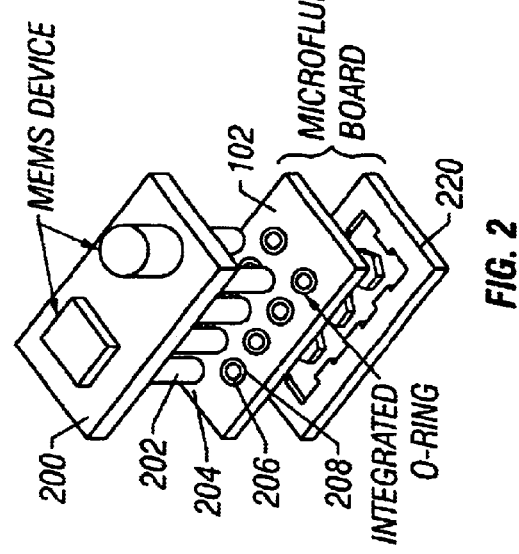
FIG. 4 shows a cross section of the rubber O-ring showing the substrate and the relationship between the substrate and the O-ring.

FIG. 4 shows a cross-sectional view of the O-ring coupler device. The substrate 401 can be any material, but is preferably a material that can be processed using semiconductor processing techniques. A preferred material, for example, might include silicon. The silicon is etched, as described herein, to form a backside hole 400, and a front hole portion 402. The front hole portion 402 may be larger in outer diameter then the backside hole 400. The O-ring device 405 is located within the backside hole 400. The O-ring device 405 is recessed within the hole, so that part of the width of the rubber O-ring abuts against the silicon substrate 401, and another part of the width of the rubber O-ring extends beyond the silicon substrate 401. FIGS. 5A and 5B show photographs of the actual device.

FIGS. 6 and 7 show the sealing mechanism of the device. Note that in both of these embodiments, the vector describing the force from the o-ring is directed towards the center of the hole. Put another way, the direction of the force vectors for embodiments are in the same general direction, i.e. towards the center of the hole. However, the location of the force vector may be different in the different embodiments.

FIG. 6 shows a first way of sealing to the o-ring couplers. In this first way, when the capillary to be connected 600 is placed within the hole 605, the rubber is deformed and wrapped against the capillary to form a tight seal. A portion 610 of the rubber o-ring is deformed to be located outside of the actual substrate 615. The deformed rubber wraps around the capillary, and may cover and make contact with the capillary over an area larger than the cross-sectional dimension 406 of the substrate. Note that the force may be primarily exerted in this embodiment in the locations shown as 625, 630, since the O portion is extended outside the perimeter defined by the substrate.

In the second embodiment, shown in FIG. 7, the sealing is achieved by a restoration force exerted by the compressed rubber O-ring while the compressed rubber O-ring stays substantially constant in its position within the substrate. The force occurs in the area of the rubber O-ring itself. Rubber O-ring 710 extends over only part of the width of the substrate 720. The force is caused by the restoration force of the compressed rubber O-ring.

A number of different materials may be used for formation of the O-ring. Each of these materials should preferably be elastomeric and provide a fairly low Young's modulus, and high elongation prior to fracture. For example, in the embodiment of FIG. 6, the elongation of the material must be 100 percent or greater.

One of the preferred materials may be silicone rubber. This material may be quite useful, since it has many different specific forms, and many different material variations. The coupler material may also be made from different materials such as silicon, metals or plastics so long as the mechanical properties are as desired, and the materials are compatible with the design of microfluidic systems. Different specific materials are also disclosed herein.

FIGS. 8A–8B show the process flow for the formation of the rubber o-ring. This formation flow represents a specific formation of a circular O-ring with an annulus width of 500 microns. The inner diameter of the O ring may vary between 400 um and 700 um, but preferably less than 1000 um or 2000 um. The thickness of the O-ring in this embodiment is selected as 250 microns, although other values may also be used. In the embodiment of FIG. 8A, the O rings are intended for capillaries of outer diameter either 860 microns or 640 microns.

The process starts with a silicon substrate in FIG. 8A. The silicon substrate is first etched to a depth shown as 800. This depth is the desired depth of the O-ring that will be formed. The etching of the annular groove 802 for the O-ring can be carried out using deep reactive ion etching to define the overall O-ring shape. Again, the O-ring shape is not limited to being annular, but can be any shape as defined for various inlet and outlet geometries. However, an annular shape will be described herein.

In FIG. 8B, an $SiO_2$ layer 810 is formed over the entire upper surface. The $SiO_2$ layer may be 2.5 microns in thickness. This layer is thermally grown to be used as the mask for later deep reactive ion etching. A one micron thick layer of silicon nitride, $SiN_x$, 812 is formed on top of the $SiO_2$ layer to serve as an adhesion layer between the substrate and the O-ring material which may be e.g. silicone rubber. This step may be desirable, because the silicone rubber that is being used herein does not exhibit good adhesion properties to $SiO_2$. In other embodiments, however, where other materials are used, this adhesion layer might not be necessary.

FIG. 8B represents inserting the silicone rubber into the cavities 802, 804. The silicone rubber may be squeezed in and squeegeed off for example. This leaves the cavity 802 filled with a silicon rubber plug.

In FIG. 8B, deep reactive ion etching is carried out from the back side of the substrate 820. This is carried out to form the back side hole 822. The back side hole may be slightly larger than the inner diameter of the annular disk formed by the cavity 802. In this way, when the final device is formed, the silicone o-ring may extend by some desired amount into the open cavity. The back side hole is etched using this $SiO_2$ as an etch stop. At FIG. 8B, the $SiO_2$ layer 810 and the silicon nitride layer are etched away using buffered HF (BHF) and $SF_6$ plasma, to leave an opening 830 with inner O ring surfaces facing the opening, and extending into the opening.

A number of different tests may be carried out on these rubber O-rings, and the results of these tests may be used to determine design characteristics for the O rings. A first observation made from the tests is that the seal between the capillary and the O-ring may be improved by increasing the area of the seal between the capillary and the O-ring. For example, the embodiment of FIG. 6 has an area that extends over a longer portion. This embodiment may provide a better seal than the embodiment of FIG. 7 in some instances. As in the embodiment of FIG. 6, the increase in area of contact can be effected by allowing the O-ring to deform.

Leak rate can also be tested. In the leak rate test, an 860 microns outer diameter tube was coupled to a 400 micron inner diameter o-ring. Under 20 PSI of pressure, virtually no leakage was detected over a 12 hour test. Table 1 shows the leak rate tests on different to diameters vs. the inner diameter of a rubber o-ring. From this, it can be determined that tight seals can be obtained when the o-ring is properly matched to the outer diameter of the capillary.

TABLE I

Leak rate test on different tube diameters vs. inner diameter of Rubber O-rings.

| Tube O.D. | Inner Diameter of Rubber Mounts Di [$\mu$m] | | | |
| --- | --- | --- | --- | --- |
| ($\mu$m) | 400 | 500 | 600 | 700 |
| 860 | Non-detectable* | Non-detectable* | Non-detectable* | Non-detectable* |
| 640 | Non-detectable* | 1.11 ml/min @ 11.5 psi | Infinite** | Infinite** |

*Non-detectable (<<0.1 $\mu$l/min @ 20 psi)
**Infinite (>>10 $\mu$l/s @ 0.5 psi)

Figure 9A:
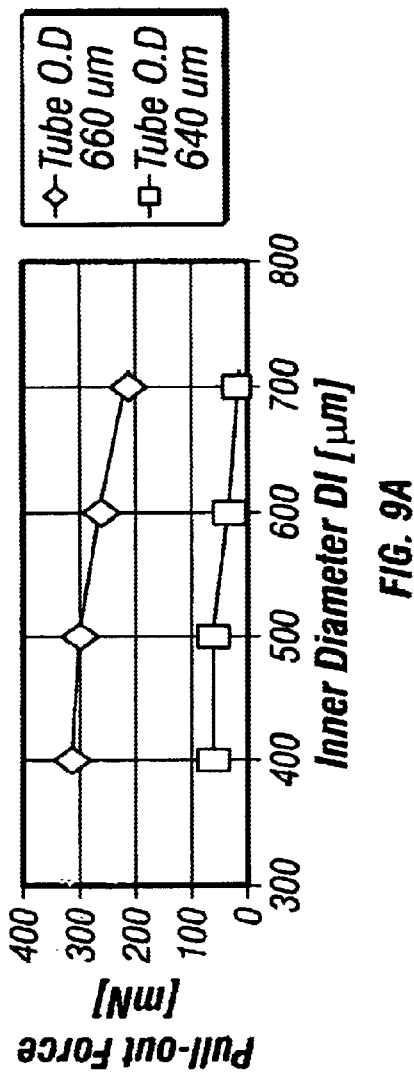
FIGS. 9a and 9b show diagrams of force versus diameter.
Figure 9B:
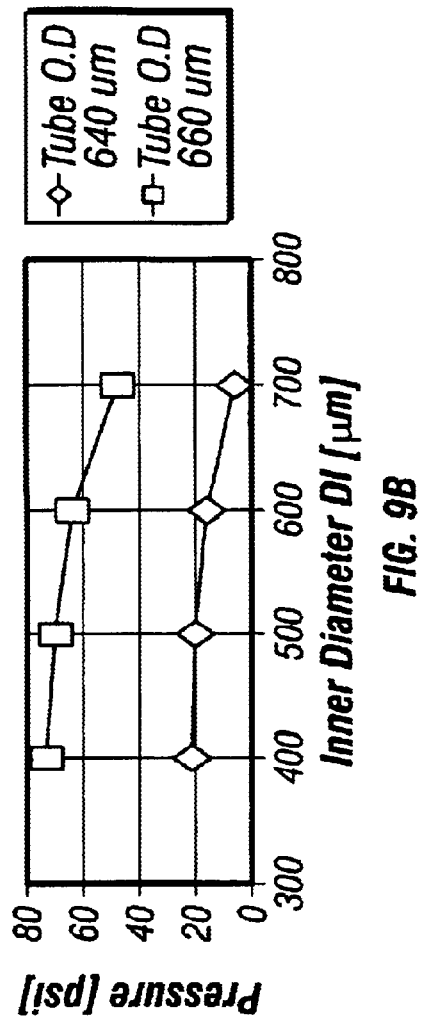

Another important Figure of merit for such devices is the pull out force. This defines a measure of how large a force is required to pull out the capillary when it is attached to the coupler. This can be detected, for example, using a load cell with a load as a function of position state. The measurements of the values will vary over the entire operation area, due to the interacting static friction coefficient with the kinematic friction coefficient. As would be expected, the force to pull the capillary out of an O-ring decreases as the O-ring inner diameter increases. FIGS. 9A and 9B show the theoretical holding pressures and pullout forces for a number of different scenarios of different tube sizes.

A reliability test may be carried out, with some cracking being noticed, but many materials withstanding a 200× operation. Different kinds of silicone rubbers may be investigated to improve the reliability.

Although only a few embodiments have been disclosed in detail above, other modifications are possible. All such modifications are intended to be encompassed within the following claims, in which:

What is claimed is:

1. A micromachined assembly, comprising:
   a substrate formed of a semiconductor material having a hole therein; and
   a sealing ring, formed of a material with a low Young's modulus and high elongation, formed in said hole, and having internal surfaces which define a flat contact portion having a flat surface extending across said substrate, said contact portion producing that produces a force towards a centerline of said hole extending over, an entire portion of said internal surfaces.

2. An assembly as in claim 1, wherein said sealing ring is formed of silicone rubber.

3. An assembly as in claim 2, wherein said sealing ring is formed in a way that allows it to deform to an area outside of said substrate when a capillary is inserted therein, wherein said force is produced in said area outside of said substrate.

4. An assembly as in claim 2, wherein said sealing ring is formed in a way that retains said sealing ring inside said substrate when a capillary is inserted therein.

5. An assembly as in claim 1, further comprising a plurality of capillaries, on another substrate, and having said same spacing as a spacing of said sealing rings, thereby allowing said plurality of capillaries to be inserted into said plurality of sealing as a unit.

6. An assembly as in claim 1, wherein said sealing ring is an O ring, and inner surfaces of said O-ring have a smaller diameter than sealing inner surfaces of said hole.

7. An assembly as in claim 1, further comprising a microfluidic element, coupled to said sealing ring.

8. An assembly as in claim 7, wherein said microfluidic element is one of a micropump, a micro valve, a micro heat exchanger, a micro mass spectrometer, a micro chromatograph, or a micro mixer.

9. An apparatus, comprising:
   a semiconductor substrate with a hole therein defining an inner surface; and
   a sealing part, of an elastomeric material, held within said hole, and having a flat surface portion which extends across a surface of said hole and provides an elongated flat surface such that said portion has a smaller diameter than the diameter of said hole, said diameter of said hole being less than 1000 microns in diameter; and
   wherein said sealing part is of a shape which deforms to an area outside of said semiconductor substrate when a tube is inserted and forms a sealing portion at least along said area outside of said semiconductor substrate.

10. A micromachine assembly, comprising:
    a substrate, formed of a semiconductor material having a plurality of holes therein;
    a plurality of tubes, having outer diameters smaller than an inner diameter of said hole; and
    a sealing ring, formed of a material with deformable properties, in one of said holes, said sealing ring formed in a way that allows the sealing ring to deforms when said tubes are inserted; an outside of said sealing ring making contact with the tube over an area larger than a cross-sectional dimension of the substrate when said tube is located inside said the hole and which produces a force toward a centerline of said hole over said area.

11. An assembly as in claim 10, wherein said sealing ring is substantially annular in shape.

* * * * *